United States Patent [19]
Young et al.

[11] Patent Number: 5,578,194
[45] Date of Patent: Nov. 26, 1996

[54] CALIBRATION OF ELECTRODES

[75] Inventors: Chung C. Young, Weston; Jeffrey Chien, Ashland; David Ferragamo, Revere; Robin A. Welch, Peabody, all of Mass.

[73] Assignee: Nova Biomedical Corporation, Waltham, Mass.

[21] Appl. No.: 402,130

[22] Filed: Mar. 10, 1995

[51] Int. Cl.[6] .................................................. G01N 27/26
[52] U.S. Cl. ........................ 205/782; 204/415; 204/431; 204/433; 205/783; 205/785.5; 205/787.5; 205/792; 436/8; 436/11; 436/68
[58] Field of Search .................................... 204/415, 431, 204/433; 205/782, 782.5, 783, 785.5, 787.5, 792; 436/8, 11, 68

[56] References Cited

U.S. PATENT DOCUMENTS

| | | |
|---|---|---|
| 3,429,784 | 2/1969 | Molloy .................................. 204/415 |
| 3,997,420 | 12/1976 | Buzza .................................... 204/415 |
| 4,001,142 | 1/1977 | Turner . |
| 4,116,336 | 9/1978 | Sorensen et al. . |
| 4,151,108 | 4/1979 | Sorensen et al. . |
| 4,279,775 | 7/1981 | Louderback et al. . |
| 4,289,648 | 9/1981 | Hoskins et al. . |
| 4,299,728 | 11/1981 | Cormier et al. . |
| 4,336,031 | 6/1982 | Hopmeier et al. . |
| 4,369,127 | 1/1983 | Cormier et al. . |
| 4,663,959 | 5/1987 | Rogge et al. . |
| 4,843,013 | 6/1989 | Chiang . |
| 4,871,439 | 10/1989 | Enzer et al. . |

*Primary Examiner*—T. Tung
*Attorney, Agent, or Firm*—Fish & Richardson P.C.

[57] ABSTRACT

A $CO_2$ electrode can be calibrated with two $PCO_2$ calibration standard solutions having known pH values and known bicarbonate ion source concentrations. An $O_2$ electrode can be calibrated using air as one calibration standard and a solution containing an excess of an $O_2$ depleting agent as a second calibration standard.

6 Claims, 2 Drawing Sheets

FLUID REAGENT POUCH

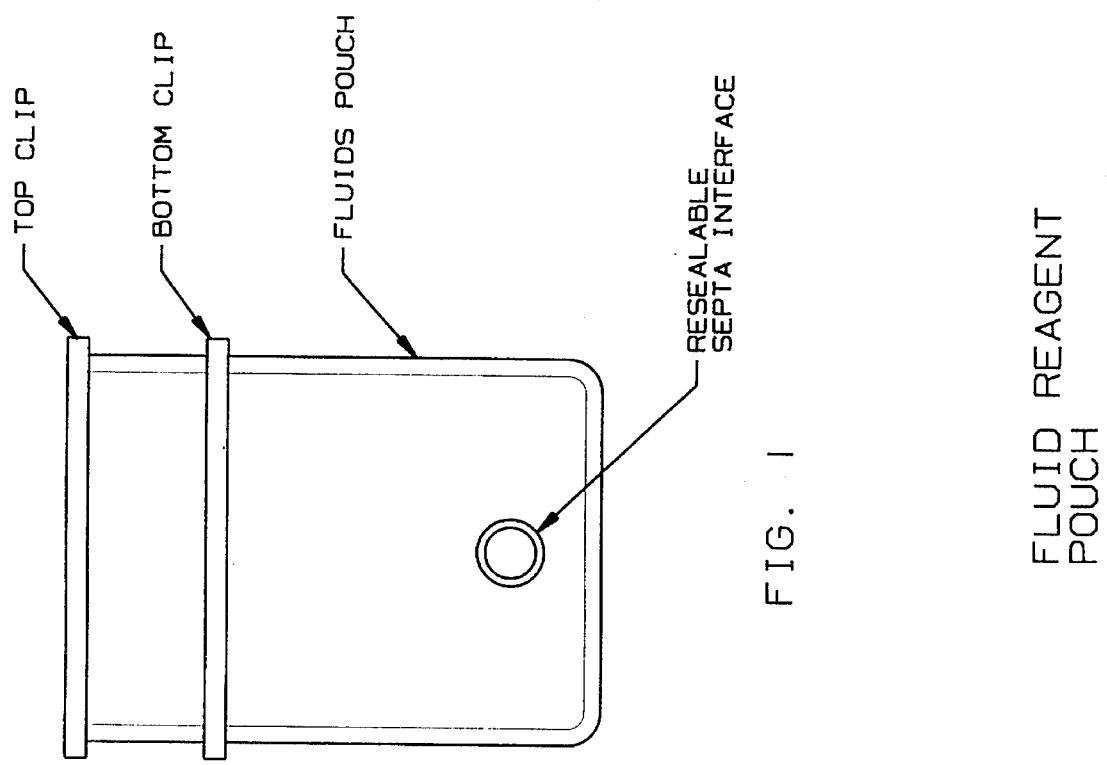

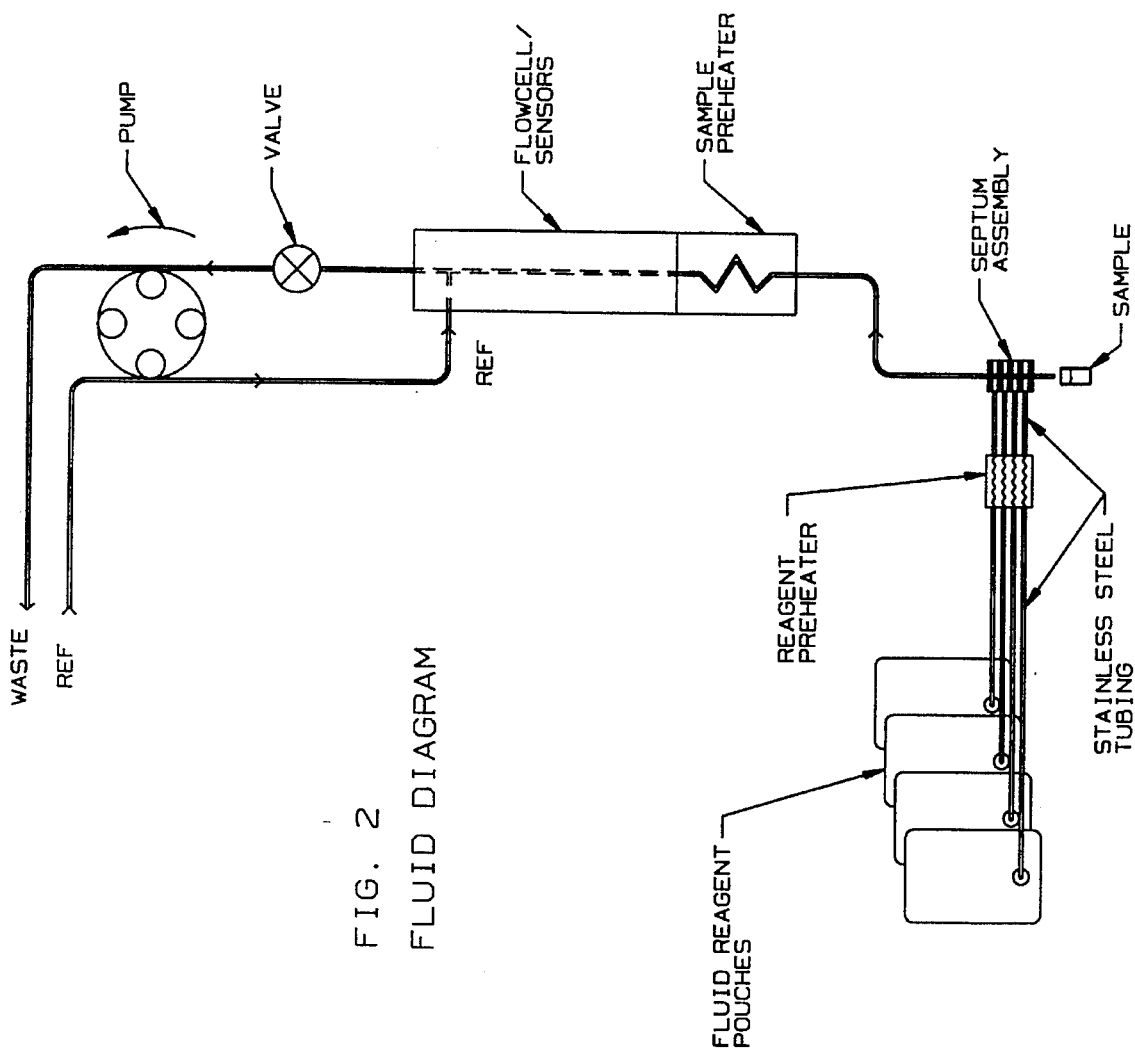
FIG. 2 FLUID DIAGRAM

CALIBRATION OF ELECTRODES

The invention relates to calibration standards or electrodes.

BACKGROUND OF THE INVENTION

Blood gas analyzers typically include electrodes that measure the pH, the partial pressure of $CO_2$ ($PCO_2$), and the partial pressure of $O_2$ ($PO_2$) of a blood sample. Such electrodes generally are calibrated prior to use on a blood sample. Calibration of an electrode involves contacting the electrode with at least two standard solutions or gases having known concentrations of the substance being analyzed (e.g., $CO_2$). The electrode provides an electrical response that is used to generate a calibration slope. The electrode then is contacted with the blood sample, generating further electrical response, and the calibration slope is used to convert this electrical response into the concentration of the substance in the blood sample, Electrodes in blood gas analyzers are calibrated periodically because the response provided by an electrode for a particular sample tends to drift (vary) with the passage of time.

Different types of standard solutions or gases have been used to calibrate $CO_2$ and $O_2$ electrodes. One type of calibration standard is generated by bubbling a dry $CO_2$ and $O_2$ gas mixture through a humidifier. If the volume fraction of $CO_2$ and $O_2$ in the dry gas mixture are known, the $PCO_2$ and $PO_2$ in the humidified gas can be calculated as follows:

$$PCO_2 = vCO_2 \times (P_{atm} - 47 \text{ mmHg})$$

$$PO_2 = vO_2 \times (P_{atm} - 47 \text{ mmHg})$$

In the equations, the $P_{atm}$ is the atmosphere pressure (which is equal to 760 mmHg at standard condition), and 47 mmHg is the saturated water vapor pressure at 37° C.

Gas tonometered aqueous solutions packaged in sealed containers also have been used as calibration standards for $CO_2$ and $O_2$ electrodes. The manufacturing environment for the gas tonometered solutions requires precise temperature and pressure control to ensure the accuracy of the calibration standards. It generally also is necessary to equilibrate these standards, external of a blood gas analyzer, to a known temperature before using them to calibrate the electrodes in the analyzer. This equilibrating process can be very time consuming depending upon the ambient temperature and the amount of standard solution in the container. It also requires complex constant temperature controlling hardware.

Other calibration standards that have been used with $CO_2$ and $O_2$ electrodes contain water, an organic solvent, and a $CO_2$ or $O_2$ complexing agent to vary $O_2$ and $CO_2$ solubility in the sample.

SUMMARY OF THE INVENTION

The invention relates to using aqueous standards to calibrate the pH, $PCO_2$, and $PO_2$ electrodes in a blood gas analyzer. The aqueous standards require no gas tonometry, no precise temperature and pressure control during manufacture, and no time-consuming temperature equilibration prior to use. The aqueous standards are relatively stable, and have a long shelf-life.

One aspect of the invention features a method of calibrating a $CO_2$ electrode. The method is based on the recognition that the $PCO_2$ of an aqueous solution can be determined if the concentration of a bicarbonate ion source in the sample and the pH of a solution are known. The method includes: (1) determining the $PCO_2$ of a first $CO_2$ calibration standard solution from the concentration of bicarbonate ion source and the pH of the first standard solution; (2) determining the $PCO_2$ of a second $CO_2$ calibration standard solution from the concentration of bicarbonate ion source and the pH of the second standard solution; and (3) calibrating a $CO_2$ electrode using the first and second $CO_2$ calibration standard solutions.

The featured method for calibrating a $CO_2$ electrode derives from the following scientific principles. The Henderson-Hasselbalch equation provides:

$$pH = pK + \log\{[HCO_3]/(\alpha \times PCO_2)\} \quad (1)$$

In the equation, K is the dissociation constant for carbonic acid and $\alpha$ (mmol/L/mmHg), the Bunson coefficient, is the solubility coefficient of $CO_2$. At 37° C., pK is 6.091 and $\alpha$ is 0.0307. By including these constants, equation (1) can be rearranged as follows:

$$PCO_2 = [HCO_3] \times 10^{(7.604-pH)} \quad (2)$$

Thus, if a known amount of $HCO_3$ exits in an aqueous solution, the $PCO_2$ in the aqueous solution can be calculated from equation (2) using the pH of the same solution measured at 37° C.

Utilizing this concept, a pair of $CO_2$ calibration standard solutions can be formulated with different pH and $HCO_3$ concentrations to provide two calibration points to calibrate the $CO_2$ electrode. The preferred $CO_2$ calibration standard solutions contain pH buffers and $NaHCO_3$ (a bicarbonate ion source). The dissolved $CO_2$ in the pH buffers is negligible before adding the bicarbonate. The $HCO_3$ concentration for each standard can be expressed as equation (3) after adding a known amount of $NaHCO_3$ salt to the buffer solution sealed in a gas impermeable container:

$$[HCO_3] = [NaHCO_3] - \alpha \times PCO_2 \quad (3)$$

Rearranging equation (2) and (3), $$PCO_2 = [NaHCO_3] \times 10^{(7.604-pH)}/\{1 + \alpha \times 10^{(7.604-pH)}\} \quad (4)$$

From equation (4), the $PCO_2$ of each $CO_2$ calibration standard solution can be calculated directly from the known $NaHCO_3$ concentration and the pH of the standard solution at 37° C. Once the $PCO_2$ of the calibration standard solutions are known, the standard solutions can be used to calibrate the $CO_2$ electrode.

The gas impermeable container can be a pouch formed by heat sealing together the flexible, gas impermeable material.

The $CO_2$ calibration standard solutions preferably are packaged in the gas impermeable container with zero head space to reduce the air contamination. Preferably, the zero head space is maintained as the reagent is consumed. For example, with the preferred pouches one end of the pouch includes a resealable system through which standard solutions can be provided to the gas tight flow path of the analyzer. As the $CO_2$ calibration standard solution in the pouch is fed to the flow path, the pouch collapses because the flow path is gas tight and as a result no volume replacement occur.

The $PCO_2$ and pH of the $CO_2$ calibration standard solutions can vary somewhat due to changes in temperature and pressure, which can cause, for example, outgassing of the $CO_2$ in the standard. Thus, the pH of each $CO_2$ calibration standard solution can be measured by the pH electrode in the blood gas analyzer. Preferably, prior to measuring the pH and the $CO_2$ of the calibration standard solution, the pH electrode is calibrated with two pH calibration standards, each of which should have a known constant pH.

A second aspect of the invention features a method of calibrating an $O_2$ electrode. The method employs two $O_2$ calibration standards. One $O_2$ calibration standard is room air, which has a $PO_2$ of approximately 150 mmHg at 1 atm. The second $O_2$ calibration standard contains an excess of an $O_2$ depleting agent, preferably $Na_2SO_3$ or $Na_2S_2O_4$, and thus has a $PO_2$ of zero. The second $O_2$ calibration standard preferably is packaged in a gas impermeable container. The featured method includes the step of calibrating an $O_2$ electrode using the first and second $O_2$ calibration standards.

Another aspect of the invention features a method of calibrating pH, $CO_2$, and $O_2$ electrodes in the same blood gas analyzer. The method includes calibrating the pH electrodes using two pH calibration standards; calibrating the $CO_2$ electrode using the first and second $PCO_2$ calibration standard solutions; and calibrating the $O_2$ electrode using the first and second $PO_2$ calibration standards. Preferably, the pH of each of the $PCO_2$ calibration standard solutions is measured by the pH electrode in the blood gas analyzer. In addition, preferably the second $PO_2$ calibration standard is also used as a pH calibration standard.

Another aspect of the invention features a method of manufacturing a calibration standard solution having a known $PCO_2$ for a $CO_2$ electrode. The method includes adding a known amount of a bicarbonate ion source to provide an aqueous solution having a known concentration of the bicarbonate ion source; sealing the aqueous solution in a gas impermeable environment; measuring the pH of the aqueous solution; and from the pH and the concentration of the bicarbonate ion source, determining the $PCO_2$ of the solution.

Another aspect of the invention features a calibration standard that can be used to calibrate a $CO_2$ electrode. The standard solution includes a known quantity of a bicarbonate ion source, and is enclosed in a gas impermeable container. Preferably the container includes substantially no head space, thus minimizing air contamination. The standard solution is further characterized in that once the pH of the standard is determined the $PCO_2$ of the standard can be accurately calculated from the pH and the concentration of the bicarbonate ion source, thus allowing the solution to be used for calibrating a $CO_2$ electrode.

A significant advantage of the present invention is that the calibration standards can be manufactured at normal conditions without needing an elaborate controlled environment, and then used to calibrate $CO_2$ and $O_2$ electrode in blood gas analyzers in which the temperature is usually maintained at 37° C. without first equilibrating the standard solutions to a known constant temperature prior to use. The effect of temperature variation can be compensated through the variation of the pH in the standard solution, which are measured during calibration by the pH electrode in the analyzer. In the case of $PO_2$ electrode calibration the room air sample aspirated into the electrode measuring site is controlled at 37° C. during system calibration, and the other $O_2$ calibration sample contains no dissolved oxygen. As a result, temperature variation of the second $O_2$ calibration standard will not affect the $PO_2$ of the sample.

Other features and advantages of the invention will be apparent from the description of the preferred embodiment thereof, and from the claims.

BRIEF DESCRIPTION OF THE DRAWING

FIG. 1 is a gas impermeable container.

FIG. 2 is a fluid flow diagram.

DESCRIPTION OF THE PREFERRED EMBODIMENTS

Blood gas analyzers typically include pH, $CO_2$, and $O_2$ electrodes. The preferred method of calibrating these electrodes employs five calibration standards.

Two standard solutions are used to calibrate the $CO_2$ electrode. Preferred $CO_2$ calibration standard solutions include a pH buffer and a known concentration of a bicarbonate ion source like $NaHCO_3$. The $CO_2$ calibration standard solutions preferably are formulated so that $PCO_2$ of one calibration standard solution is at normal level of approximately 40 mm Hg, and the $PCO_2$ of the second calibration standard solution is towards the high end of the range (approximately 70 mm Hg). The calibration standards preferably are buffered to a pH of between 6 and 8. Biological buffers such as phosphates, MES, HEPES, MOPSO and Tris buffers can be used.

Two additional calibration standards are used to calibrate the pH electrode. Any conventional pH calibration standard can be used. One standard preferably has a pH that is at normal level of approximately 7.4, and the other sample has a pH that is approximately 6.8. The standards preferably include conventional buffer systems such as phosphate, HEPES, MES, MOPSO, and Tris buffers.

Preferably, one of the two pH calibration standards also serves as an $O_2$ calibration standard. To accomplish this, an excess of an $O_2$ depleting agent is added to one of the pH calibration standards, so that the standard has a $PO_2$ of zero. Preferred $O_2$ depleting agents include $Na_2S_2O_4$, $Na_2SO_3$, ascorbic, or other reducing agents.

The second calibration standard is air, which has a $PO_2$ of 150 mmHg at atmospheric pressure.

A preferred set of calibration standards (excluding air) for use in calibrating $PCO_2$, $PO_2$, and pH electrodes in blood analyzers is provided in Table 1. Solutions A and B are the $PCO_2$ calibration standards; solutions C and D are the pH calibration standards; and solution D also is a $PO_2$ calibration standard.

TABLE I

| Chemical | A | B | C | D |
| --- | --- | --- | --- | --- |
| NaCl, mmol/L | 80 | 9 | 110 | 24 |
| HEPES Acid, mmol/L | 56 | — | 56 | — |
| 1N NaOH, mL/L | 30 | — | 30 | — |
| KCl, mmol/L | 4 | 10 | 4 | 10 |
| MOPSO, mmol/L | — | 33 | — | 33 |
| MOPSONa, mmol/L | — | 48 | — | 48 |
| NaHCO$_3$, mmol/L | 20 | 15 | — | — |
| Na$_2$S$_2$O$_4$, mmol/L | — | — | — | 2 |

The relevant calibration concentrations corresponding to each of the above solutions are provided below in Table 2:

TABLE II

| Chemistry | Concentrations Standards |
| --- | --- |
| pH | C(7.38), D(6.84) |
| PCO$_2$ | A(≈30 mmHg), B(≈65 mmHg) |
| PO$_2$ | D(0 mmHg), Air(150 mmHg) |

The actual $PCO_2$ in solutions A and B are calculated using equation 4 after the pH measurements for solutions A and B are completed during the calibration cycle. The actual calculated $PCO_2$ values in both solutions A and B are then used to calculate the Nernestian slope of the $PCO_2$ electrode.

The calibration standards, and in particular standard solutions A, B, and D, are stored in separate gas impermeable containers, preferably pouches, that include substantially no head space.

A preferred pouch is illustrated in FIG. 1. The pouch can be made of any gas impermeable material. Preferred pouch materials include VAPOR LOC (VF-52, POLYESTER POLYESTER/LDPE/FOIL/LDPE/LLDPE), LUDLOW LAMINATION (MARVEL SEAL 360, BLAX NYLON FILM/LDPE/FOIL/LDPE/EVA BLEND) and BP/BXL PLASTICS (AA 601/100, AA 601/120, AA 601/150, LLDPE/TIE LAYER/EVOH/TIE LAYER/LLDPE). The bottom end of the pouch includes a re-sealable septum 10. The top of the pouch has been heat sealed. To prevent the outgassing of $CO_2$ in solutions A and B and the air contamination by $O_2$ in standard D during solution preparation, concentrated $NaHCO_3$ and $Na_2S_2O_4$ solutions are prepared separately and stored in the gas tight glass syringes. The pouch is sealed by a pair of clips at two pre-marked head spaces as illustrated in FIG. 1 after filling the pouch with the standard with no $NaHCO_3$ (solutions A and B) or $Na_2S_2O_4$ (solution D) added. The bottom clip is positioned right at the fluid level to ensure zero headspace in the pouch. The air between two clips is vacated by collapsing that portion of the pouch before the top clip is positioned to the mark. The bottom clip is then removed before the concentrated $NaHCO_3$ or $Na_2S_2O_4$ solution is injected into the pouch through the resealable septum at the bottom of the pouch. The amount of solution injected is pre-calculated to provide accurate ingredients for the formulation and to fill the pouch to the top clip positions, creating a near zero head space within the pouch.

The preferred calibration solutions can be used to calibrate the pH, $CO_2$, and $O_2$ electrodes in typical blood gas analyzers. The main components of a preferred analyzer are referred to in FIG. 2, which generally sets out a preferred fluid flow path through the analyzer. The main components are some combination of electrodes, including pH, $CO_2$, and $O_2$ electrodes; a peristaltic pump to drive the fluid flow through the system; a solenoid valve to stop the fluid flow before the chemistry measurement; a sampler with a septa assembly to withdraw the patient blood sample and calibration standards; a flowcell assembly to house the measuring electrodes; and a sample preheater and an air bath compartment designed to maintain the temperature at 37° C. in the flowcell assembly. To prevent the gas loss or contamination during the reagent transportation within the system, a gas tight conventional Leur-lock, is used for the inter-connection between the septum on the pouch illustrated in FIG. 1 and the gas impermeable tubing (e.g., stainless steel) which connects the fluid flow to the sampler and septa assembly.

The fluid movement is controlled by a set of microprocessor processed measuring sequences that coordinate the function of electro-mechanical components. The following are the key sequences for providing the measurement of blood chemistry. The sequences can be used with the preferred calibration standards (see Table 1):

i) Idle Sequence

System will stay idled if not in busy status.

System will also return to idle status at the end of each calibration and analysis sequence. The idle sequence includes the aspiration of calibration standard A into the flowcell assembly.

ii) Calibration Sequence

By controlling the pump and sampler movement, calibration standards A, B, C, and D, and air are aspirated into the flowcell assembly and measured by the corresponding electrodes as listed in TABLE II. The performance slope for each electrode is established after a successful calibration.

iii) Analysis Sequence

A blood sample is aspirated into the flowcell assembly and measured. After the wash cycle using calibration standard C, calibration standard A is brought into the flowcell assembly and measured. These two measurements provide the pH, $PCO_2$ and $PO_2$ results of the sample.

The chemistry tests provided in this invention can be expanded to match the NOVA STAT PROFILE 9 PLUS blood gas analyzer (pH, $PCO_2$, $PO_2$, Na, K, Cl, Ca, glucose, lactate and Hct) with proper modification of the calibration standards. No pressurized gas tanks are needed in this invention.

Other embodiments are within the claims.

What is claimed is:

1. A method of calibrating a $CO_2$ electrode in a blood gas analyzer, comprising (a) providing a first $CO_2$ calibration solution comprising water and a predetermined concentration of a bicarbonate ion source;

(b) measuring the pH of said first $CO_2$ calibration solution in said blood gas analyzer;

(c) determining the $PCO_2$ of said first $CO_2$ calibration solution from said predetermined concentration of bicarbonate ion source in said first $CO_2$ calibration solution and said pH of said first $CO_2$ calibration solution;

(d) providing a second $CO_2$ calibration solution comprising water and a predetermined concentration of a bicarbonate ion source;

(e) measuring the pH of said second $CO_2$ calibration solution in said blood as analyzer;

(f) determining the $PCO_2$ of said second $CO_2$ calibration solution from said predetermined concentration of bicarbonate ion source in said second $CO_2$ calibration solution and said pH of said second $CO_2$ calibration solution;

(g) contacting said $CO_2$ electrode with said first $CO_2$ calibration solution to generate a first electrical response;

(h) contacting said $CO_2$ electrode with said second $CO_2$ calibration solution to generate a second electrical response; and (i) generating a calibration slope for said $CO_2$ electrode using said first electrical response and said second electrical response.

2. The method of claim 1, wherein said first $CO_2$ calibration solution and said second $CO_2$ calibration solution prior to use are stored in separate gas impermeable containers.

3. The method of claim 2, wherein said gas impermeable containers comprise collapsible pouches including substantially no head space.

4. The method of claim 3, wherein said collapsible pouches each include a resealable septum through which the $CO_2$ calibration solution can be removed without introducing air into the collapsible pouch.

5. The method of claim 4, wherein the pH is measured with a pH electrode, said method further comprising:

(j) contacting said pH electrode with a first pH calibration solution having a known pH to generate a third electrical response (k) contacting said pH electrode with a second pH calibration solution having a known pH to generate a fourth electrical response; and (l) generating a calibration slope for said pH electrode using said third electrical response and said fourth electrical response.

6. The method of claim 1, wherein said bicarbonate ion source is sodium bicarbonate.

* * * * *